(12) United States Patent
Blanquaert et al.

(10) Patent No.: US 10,973,951 B2
(45) Date of Patent: Apr. 13, 2021

(54) METHOD FOR GRAFTING A BIOACTIVE POLYMER ONTO IMPLANTS

(71) Applicant: LES LABORATOIRES OSTEAL MEDICAL, Roissy Aeroport CDG (FR)

(72) Inventors: Daniel Blanquaert, Paris (FR); Bertrand De Lambert, Senlis (FR)

(73) Assignee: LES LABORATOIRES OSTEAL MEDICAL, Roissy en France (FR)

( * ) Notice: Subject to any disclaimer, the term of this patent is extended or adjusted under 35 U.S.C. 154(b) by 229 days.

(21) Appl. No.: 15/769,447

(22) PCT Filed: Oct. 18, 2016

(86) PCT No.: PCT/FR2016/052682
§ 371 (c)(1),
(2) Date: Apr. 19, 2018

(87) PCT Pub. No.: WO2017/068272
PCT Pub. Date: Apr. 27, 2017

(65) Prior Publication Data
US 2018/0243470 A1    Aug. 30, 2018

(30) Foreign Application Priority Data
Oct. 22, 2015 (FR) .................................... 15 60108

(51) Int. Cl.
*B05D 1/18*  (2006.01)
*A61L 27/16*  (2006.01)
(Continued)

(52) U.S. Cl.
CPC .............. *A61L 27/16* (2013.01); *A61L 27/06* (2013.01); *A61L 27/50* (2013.01); *A61L 27/54* (2013.01);
(Continued)

(58) Field of Classification Search
None
See application file for complete search history.

(56) References Cited

U.S. PATENT DOCUMENTS 6,497,916 B1 * 12/2002 Taylor ..................... B05C 3/09
427/2.24
9,585,780 B2 * 3/2017 Pacetti .................... A61F 2/915
(Continued)

FOREIGN PATENT DOCUMENTS

EP      2 032 663 A2      3/2009
WO      2007/141460 A2   12/2007

OTHER PUBLICATIONS

Helary et al. A bioactive polymer grafted on titanium oxide layer obtained by electrochemical oxidation. Improvement of cell response. J. Material Science Material Med 21:655-663 (Year: 2010).*
(Continued)

*Primary Examiner* — Cachet I Proctor
(74) *Attorney, Agent, or Firm* — Sughrue Mion, PLLC

(57) ABSTRACT

A method of grafting a bioactive polymer on implants, the method comprising the following steps:
  a) mounting implants on a support structure;
  b) dipping the implants in a bath of acid;
  c) rinsing the implants;
  b) dipping the implants in an anodizing bath so as to anodize them;
  e) rinsing the implants;
  f) putting the implants into a polymerization chamber;
  g) mounting the implants on an elevator present in the chamber;
  h) actuating the elevator so as to dip the implants into a polymerization bath;
  i) subjecting the polymerization bath to a polymerization catalyst;
  j) raising the elevator from the polymerization bath;
(Continued)

k) removing the implants from the elevator;
l) extracting the implants from the chamber;
m) washing the implants so as to remove any excess non-grafted bioactive polymer therefrom; and
n) drying the grafted implants.

13 Claims, 10 Drawing Sheets

(51) Int. Cl.

| | | |
|---|---|---|
| *C08F 292/00* | (2006.01) | |
| *A61L 27/06* | (2006.01) | |
| *A61L 27/54* | (2006.01) | |
| *B05D 3/06* | (2006.01) | |
| *B05D 3/00* | (2006.01) | |
| *B05D 7/14* | (2006.01) | |
| *C25D 11/26* | (2006.01) | |
| *A61L 27/50* | (2006.01) | |
| *C09D 4/06* | (2006.01) | |

(52) U.S. Cl.
CPC ............... *B05D 1/18* (2013.01); *B05D 3/007* (2013.01); *B05D 3/067* (2013.01); *B05D 7/14* (2013.01); *C08F 292/00* (2013.01); *C09D 4/06* (2013.01); *C25D 11/26* (2013.01); *A61L 2420/02* (2013.01)

(56) References Cited

U.S. PATENT DOCUMENTS

| | | | | |
|---|---|---|---|---|
| 9,855,577 | B1* | 1/2018 | Belfance | A61L 31/08 |
| 2007/0209947 | A1* | 9/2007 | Shrivastava | C25F 3/16 |
| | | | | 205/662 |
| 2009/0318622 | A1* | 12/2009 | Migonney | C08F 291/00 |
| | | | | 525/326.6 |
| 2011/0100293 | A1* | 5/2011 | Abbasian | A61L 29/085 |
| | | | | 118/696 |

OTHER PUBLICATIONS

International Preliminary Report on Patentability dated Apr. 26, 2018 issued by the International Bureau in application No. PCT/FR2016/052682.

Gérard Hélary et al., "A bioactive polymer grafted on titanium oxide layer obtained by electrochemical oxidation. Improvement of cell response", J Mater Sci: Mater Med, 2010, pp. 655-663, vol. 21, No. 2.

Bangcheng Yang et al., "Preparation of bioactive titanium metal via anodic oxidation treatment", Biomaterials, Mar. 2004, pp. 1003-1010, vol. 25, No. 6.

Kakoli Das et al., "Surface modifications and cell-materials interactions with anodized Ti", Acta Biomaterialia, Jun. 2007, pp. 573-585, vol. 3, No. 4.

International Search Report of PCT/FR2016/052682 dated Jan. 12, 2017 [PCT/ISA/210].

* cited by examiner

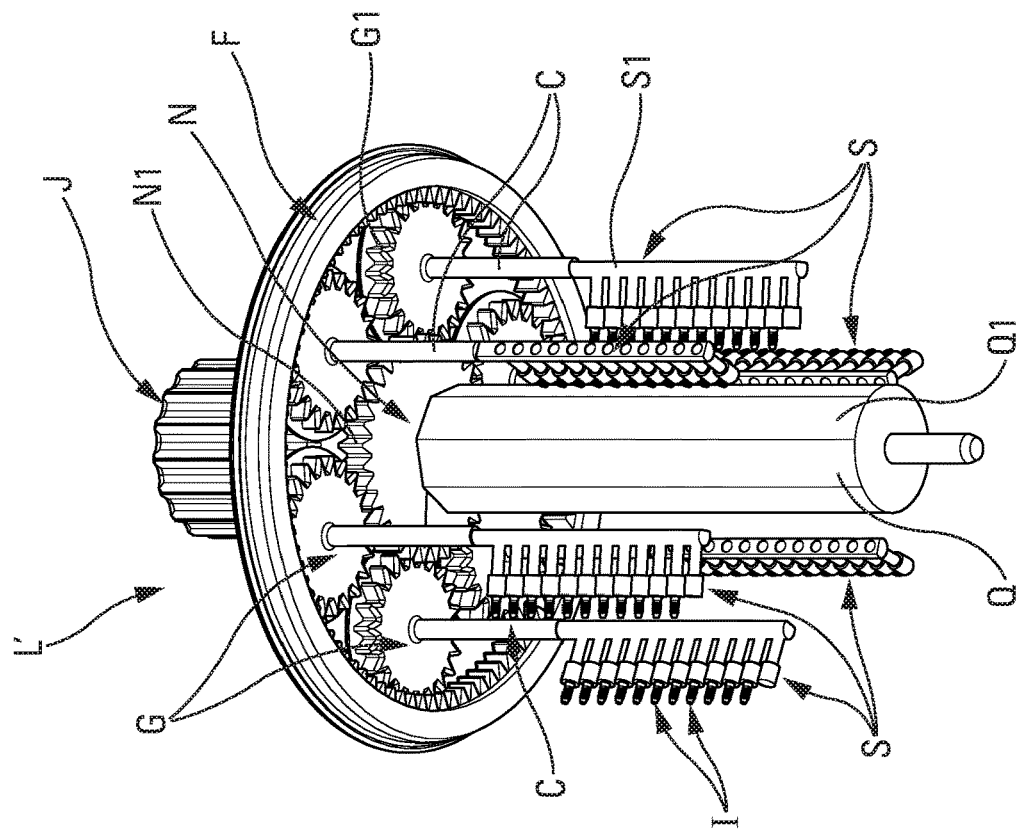
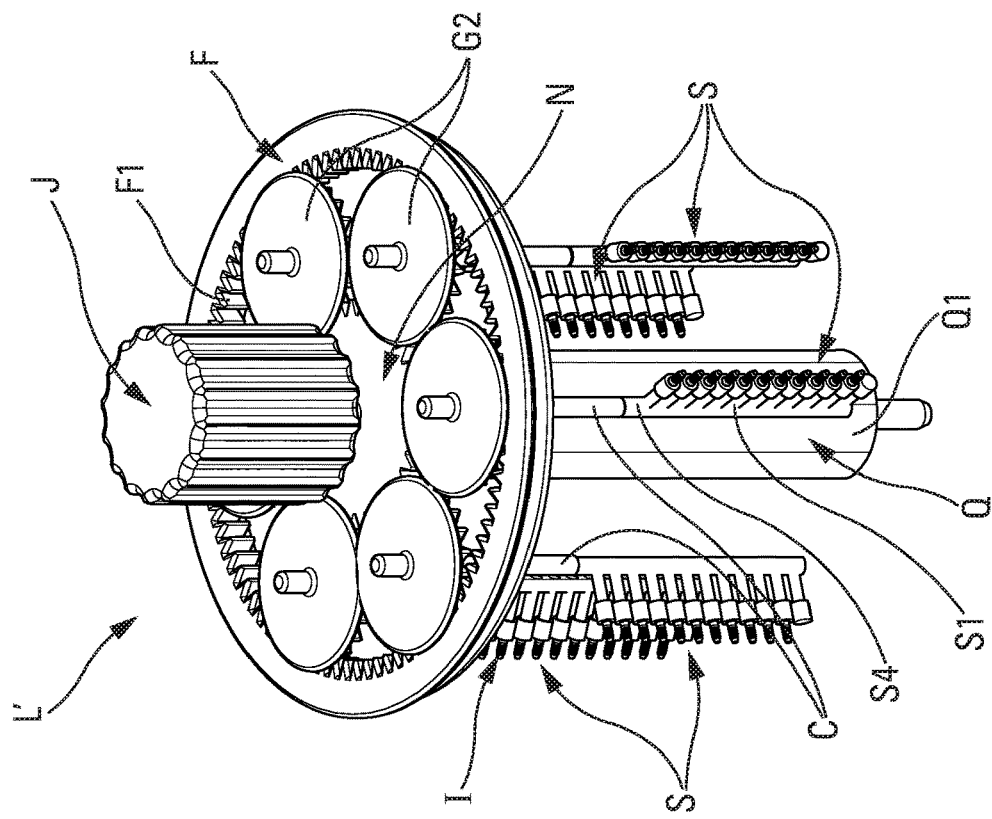

METHOD FOR GRAFTING A BIOACTIVE POLYMER ONTO IMPLANTS

CROSS REFERENCE TO RELATED APPLICATIONS

This application is a National Stage of International Application No. PCT/FR2016/052682, filed Oct. 18, 2016, claiming priority based on French Patent Application No. 1560108, filed Oct. 22, 2015

The present invention relates to a method of grafting a bioactive polymer, such as poly sodium styrene sulfonate (PolyNaSS) on implants, in particular implants made of titanium or titanium alloy. The term implants should be understood to mean any part, group of parts, or devices for being implanted, in part or in full, in a human or animal body. By way of example, mention may be made of dental implants, hip prostheses, knee prostheses, shoulder prostheses, intervertebral cages, pacemakers, etc.

In the prior art, document EP 2 032 663 is known, which describes a method of grafting bioactive polymer onto a prosthetic material made of titanium or titanium alloy. That method recommends three successive steps, namely:

generating free-radical-donating species at the surface of the prosthetic material;
generating radicals at the surface of the prosthetic material by thermal reactions; and
putting prosthetic material into contact with at least one monomer carrying a function for enabling radical polymerization. Radical polymerization of said monomer enabling the formation of a bioactive polymer in the absence of oxygen.

Consequently, the method of document EP 2 032 663 is more particularly directed to the physical or chemical reactions and interactions that make it possible to synthesize the bioactive polymer directly on the surface of an implant. This gives the bioactive polymer the characteristic of being grafted in permanent manner on the implant. The bioactive polymer is preferably PolyNaSS, and the type of oxidation of the implant is preferably chemical oxidation.

Although the method of document EP 2 032 663 outlines how to perform the grafting method in a laboratory on a small scale, it gives absolutely no indication about how to apply the grafting method industrially on a large scale.

Specifically, an object of the present invention is to use the method of grafting bioactive polymer industrially on a large scale. In other words, the grafting method is to be used in an industrial environment in order to process large numbers of implants simultaneously. Although chemical oxidation is emphasized in the grafting method of document EP 2 032 663, it quickly becomes clear in an industrial environment that oxidation of that type (chemical) is entirely inappropriate, and indeed dangerous. The present invention has thus turned to anodic oxidation (anodizing), which is not mentioned in document EP 2 032 663.

In order to industrialize the method of grafting bioactive polymer, the present invention proposes the following successive steps:

a) mounting implants on an implant support structure;
b) dipping the implants into a bath of acid so as to clean them;
c) rinsing the implants;
d) dipping the implants in an anodizing bath so as to anodize them;
e) rinsing the implants;
f) putting the implants into a polymerization chamber filled with inert gas, such as argon;
g) mounting the implants on an elevator present in the chamber;
h) actuating the elevator so as to dip the implants into a polymerization bath present in the chamber;
i) subjecting the polymerization bath to a polymerization catalyst so as to synthesize bioactive polymer on the implants;
j) raising the elevator so as to extract the implants from the polymerization bath;
k) removing the implants from the elevator;
l) extracting the implants from the chamber;
m) washing the implants so as to remove any excess non-grafted bioactive polymer therefrom; and
n) drying the grafted implants.

This succession of steps makes it possible to perform on an industrial scale the grafting method, which uses anodic oxidation (anodizing). Most of the steps are essential, even indispensable, for performing the method of grafting bioactive polymer on an industrial scale in a manner that is reproducible, effective, quick, and reliable.

Secondary or additional steps may be implemented to further improve the industrial nature of the grafting method.

The spirit of the present invention is to industrialize a method of grafting bioactive polymer that is already known from document EP 2 032 663, in order to be able to process, on a large scale and at a high rate, various implants, such as dental implants or femoral hip implants, for example.

The invention is described more fully below with reference to the accompanying drawings, which show several embodiments of the invention.

In the figures:

FIG. 5b is a large-scale perspective view of a detail of FIG. 5a;

FIGS. 9a and 9b are perspective views of another embodiment of the polymerization station;

Figure 1:
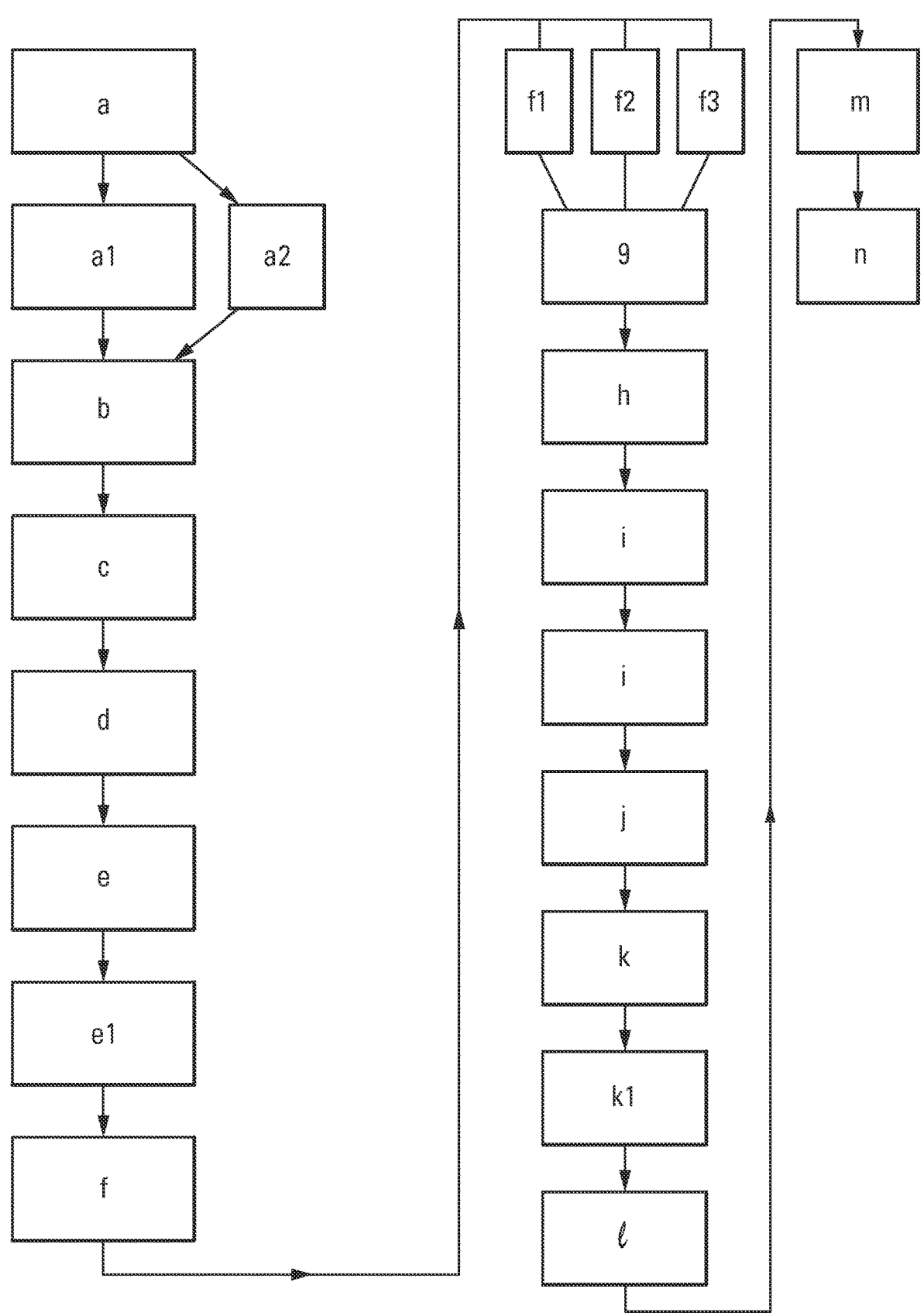
FIG. 1 is a very diagrammatic block diagram view showing the various steps of the grafting method of the invention.

Reference is made firstly to FIG. 1 in order to describe the various successive steps of the method of grafting a bioactive polymer, such as PolyNaSS, on implants, in particular implants made of titanium or titanium alloy, in order to achieve a non-stick or "non-cling" coating on which bacteria and other infectious agents slide so that they cannot develop thereon.

The major successive steps are as follows:
a) mounting implants on an implant support structure: a support element for dental implants and a support bracket for femoral hip implants are described below;
b) dipping the implants (mounted on their support) into a bath of acid, such as nitric and/or hydrofluoric acid, so as to clean them: the immersion time may lie in the range about 30 seconds (s) to 1 minute (min);
c) rinsing the implants, e.g. with water;
d) dipping the implants (mounted on their support) in an anodizing bath, e.g. based on orthophosphoric acid, so as to anodize them and thus create titanium peroxides on their surfaces: the dipping time may lie in the range about 10 s to 1 min;
e) rinsing the implants, e.g. with water;
f) putting the implants (still mounted on their support, or on some other support, or on no support) into a gastight polymerization chamber filled with inert gas, such as argon: some other inert gas could also be used;
g) mounting the implants (mounted on their support, or on some other support, or on no support) on an elevator installed in the gastight chamber;
h) actuating the elevator so as to dip the implants into a polymerization bath, e.g. a bath of monomer, such as sodium styrene sulfonate (NaSS), present in the chamber;
i) subjecting the polymerization bath to a polymerization catalyst, e.g. a thermal or UV catalyst, so as to synthesize bioactive polymer on the surface of the implants, and thus obtain an implant coated with a layer of grafted polymer, e.g. PolyNaSS;
j) raising the elevator so as to extract the coated implants from the polymerization bath;
k) removing the implants from the elevator;
l) extracting the implants from the gastight chamber;
m) washing the implants, e.g. by spraying pure water, so as to remove any excess non-grafted bioactive polymer therefrom; and
n) drying the grafted implants.

In addition to these major steps, the method also defines intermediate, secondary, and/or optional steps that further improve the major steps, or that make it easier to handle particular implants, such as dental implants or femoral hip implants, for example. In particular, mention can be made of the following steps.

For dental implants:
an intermediate step a1- between step a- and step b- that consists in mounting a plurality of implants on support elements that are themselves mounted on a support slab that advantageously includes a removable handle, the slab together with its implant support elements constituting an implant support structure;
during steps b- to f-, the implants are handled by means of the support slab, with the implant support elements mounted thereon;
an intermediate step e1- between step e- and step f- that consists in placing the support slab with its implant support elements in a container filled with inert gas, such as argon, that is advantageously provided with a gastight lid, the container then being put, during step f-, into the gastight chamber filled with inert gas, such as argon, the container then being opened so as to extract the support slab therefrom, together with its implant support elements;
an intermediate step f1- between step f- and step g- that consists in removing the implant support elements from the support slab, then in mounting the implant support elements on a support plate that is then mounted on the elevator, or, in a variant, an intermediate step f2- between step f- and step g-, step f2- consisting in mounting either the support slab (B) or the support elements (S) on vertical axial rods (C) of the elevator (L') that are rotated in the polymerization bath;
an intermediate step k1- between step k- and step l—that consists in removing the implant support elements from the elevator, then in mounting the implant support elements on a central pole that forms mounting housing for the implant support elements in order to form a washing rack that is then extracted from the chamber. The washing rack may also be formed at the outlet of the gastight chamber; and
during steps m- and n-, the implant support elements are configured in the form of the washing rack.

For femoral hip implants:
an intermediate step a2- between step a- and step b- that consists in mounting a plurality of implants (H) on a support bracket (Th), the implants (H) being handled, during steps b- to f-, by means of the support bracket (B);
an intermediate step f3- between step f- and step g- that consists in mounting the implants side-by-side on a strip that is then mounted on the elevator;
during step l-, the implants are on the strip; and
during steps m- and n-, the implants are arranged on a washing tray.

By way of example, this method of grafting active polymer is now used on dental implants for which tools, accessories, or instruments have been developed, enabling handling to be easier, quicker, and on a large scale.

Figure 2A:
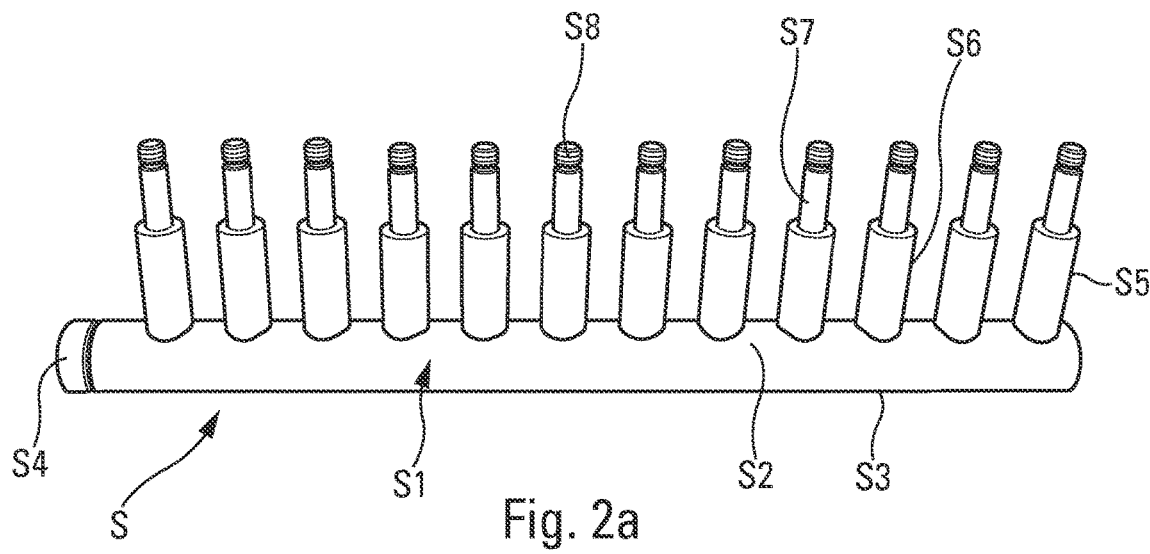
FIG. 2a is a perspective view of an implant support element of the invention.
Figure 2B:
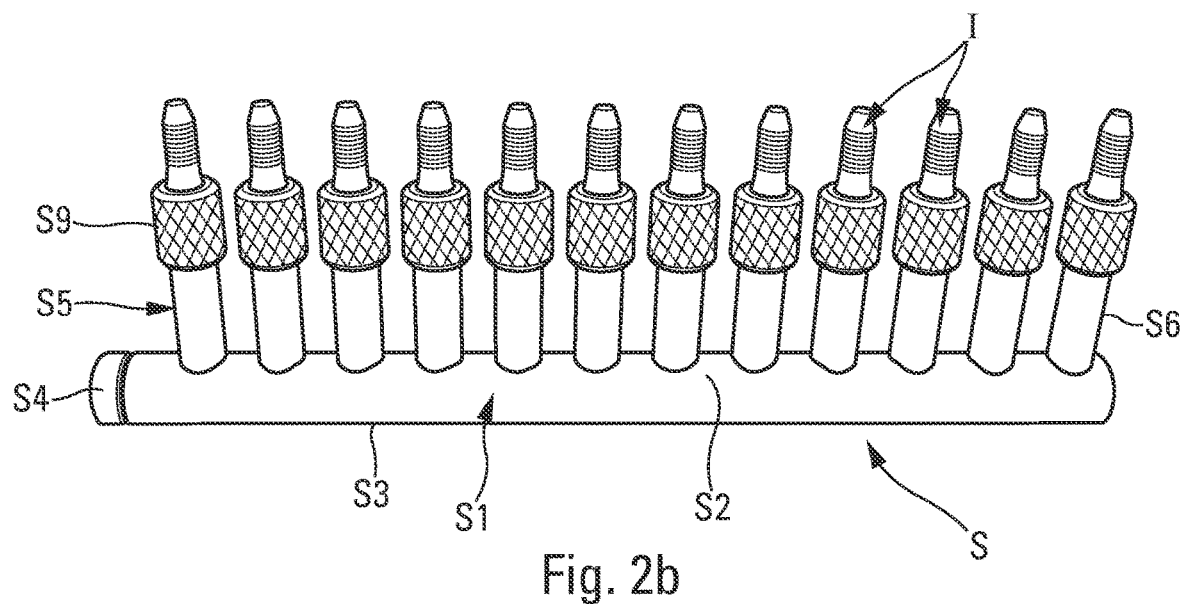
FIG. 2b is a view of the FIG. 2a implant support element with implants mounted thereon.
Figure 2C:
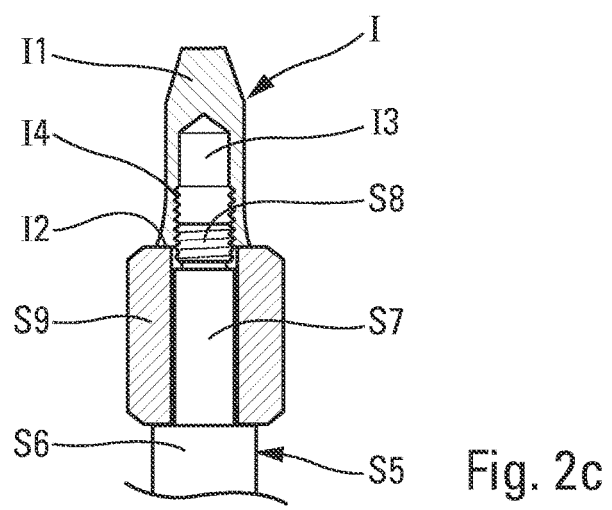
FIG. 2c is a large-scale vertical section view through an implant mounted on a pin of the implant support element in FIGS. 2a and 2b.

FIGS. 2a, 2b, and 2c show a support element S for implants, such as dental implants I. One type of implant I can be seen more particularly in section in FIG. 2c. It can be seen that the implant I comprises a head I1 at its top end, and an annular bottom edge I2 at its opposite end. The implant I defines a hollow inside 13 that presents a threaded wall 14. This design is entirely conventional for a dental implant. The support element S includes a bar S1 on which there are mounted a plurality of pins S5 that advantageously extend parallel to one another. By way of example, it is possible to provide twelve pins S5 that are arranged in alignment and in parallel on a bar S1, with the pin axes at a spacing that lies in the range about 1 cm to 2 cm. In an advantageous embodiment, the bar is cylindrical presenting a cross-section that is circular and truncated at its base in such a manner as to form a longitudinal flat that is arranged remote from the pins S5. This can be seen more clearly in FIG. 3. The bar S1 includes at least one mounting end for mounting the bar on a support structure that is defined below. The mounting end S4 may even present a hollow housing. Each of the pins S5 comprises a base S6 that is fitted to the bar S1, and a rod S7 that is mounted on the base S5, defining a bottom diameter and including a free end that is provided with a thread S8.

A shoulder is thus formed at the top end of the base around the rod S7. Each pin S5 is further provided with a rotary ring S9 that is engaged around the rod S7, bearing against the base S5. The threaded free end S8 projects out from the rotary ring S9 in order to enable the implant I to be screw-fastened on the threaded free end, coming into abutment against the rotary ring S9, as shown in FIG. 2c. It can clearly be seen that the threaded free end S8 is engaged with the internal thread 14 of the hollow housing 13 of the implant I. It suffices that the implant I is screw-fastened on the threaded free end S8 just barely enough to guarantee it is held on the rod S7, bearing against the rotary ring S9. Support elements S with the implants I mounted thereon, as shown in FIG. 2b, present the general configuration of a comb, with teeth constituted by pins S5 on which the implants I are mounted.

In the invention, the rotary rings S9 constitute a removal system for removing the implants from the reception means of the support element constituted by the threaded free ends S8. Specifically, by causing the rotary rings S9 to turn freely about the rods S7, the implants I loosen and unscrew from the threaded top ends S8, and this without any need to come into contact with the implants I, and in particular with their exposed portions. In other words, the rotary rings make it possible to unscrew the implants without needing to touch them. It is advantageous for the rotary rings S9 to be well aligned, so that it is possible to take action in common simultaneously on all of the rotary rings, so as to unscrew all of the implants I simultaneously from an implant support element S. By way of example, it is possible to envisage a rectilinear rod that is put into bearing contact with all of the rotary rings S9, and to which a rapid back and forth movement is imparted, making it possible to unscrew the implants I. The implants I can then fall by gravity into a collection container. Clearly, the removal operation for removing the implants I takes place only at the end of the grafting method, after the drying step n.

Without going beyond the ambit of the invention, it is also possible to envisage that the implants I do not have an internal thread 14, and that the bar S1 and the pins S5 are hollow so as to make it possible to generate suction that pulls the implants I against the free ends of the rods S7. By way of example, suction may be created at the mounting end S4. In this configuration, it is not necessary to provide a removal system, such as the rotary rings S9. However, applying suction is more complicated to implement, which is why the use of rotary rings S9 is simpler to perform and more effective.

Figure 3:
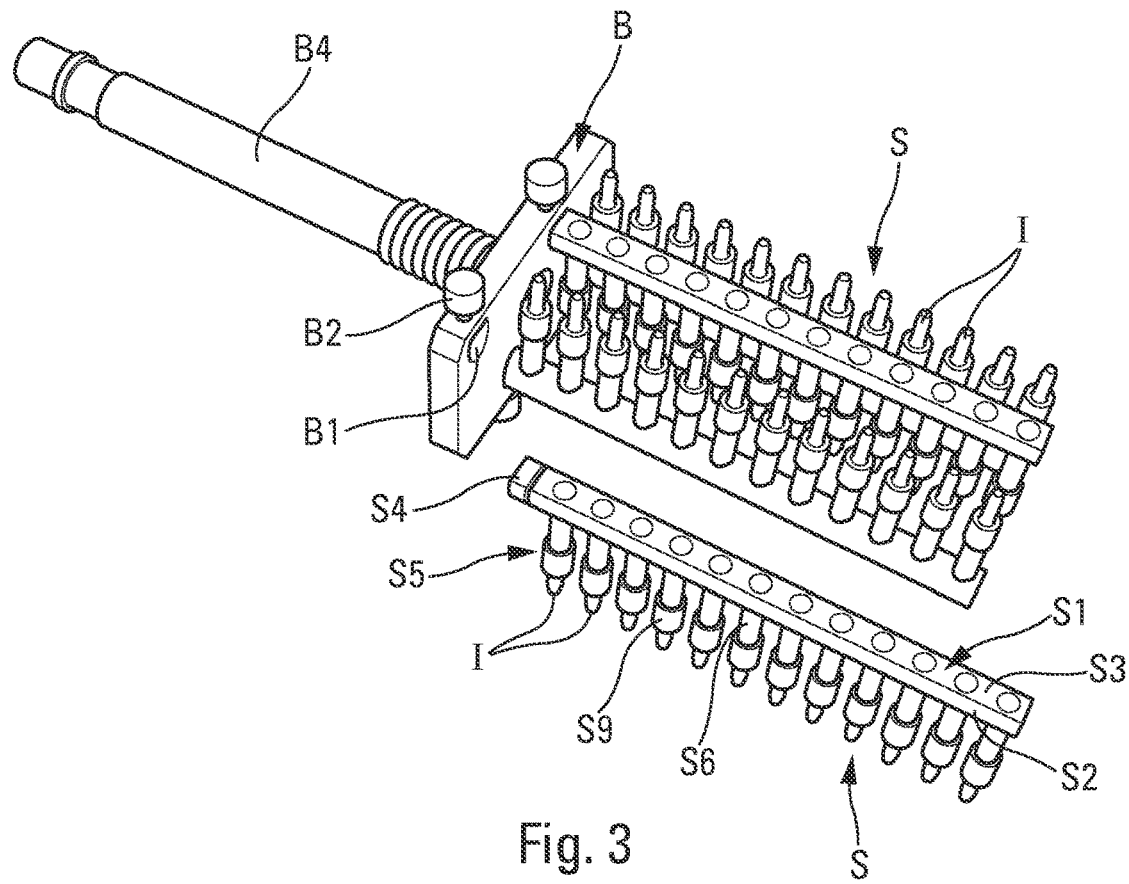
FIG. 3 is a perspective view of a mounting slab for implant support elements that has already received three implant support elements and that is ready to receive a fourth element.

FIG. 3 shows three support elements S mounted on a mounting slab B that includes a plurality of mounting housings B1 in which the mounting ends S4 of the support elements S are received and advantageously blocked by means of blocking screws B2. FIG. 3 also shows a fourth support element S that is ready to be received in its still-free mounting housing B1. Thus, four support elements S can be mounted on a mounting slab and arranged opposite ways round. Specifically, the two uppermost support elements S are arranged with their pins S5 facing downwards, while the other two support elements S mounted at the bottom are arranged with their pins S5 facing upwards. In the invention, the mounting slab B is provided with a removable stick-shaped handle B4 that makes it easy to handle the mounting slab B with its support elements S mounted thereon.

Figure 4:
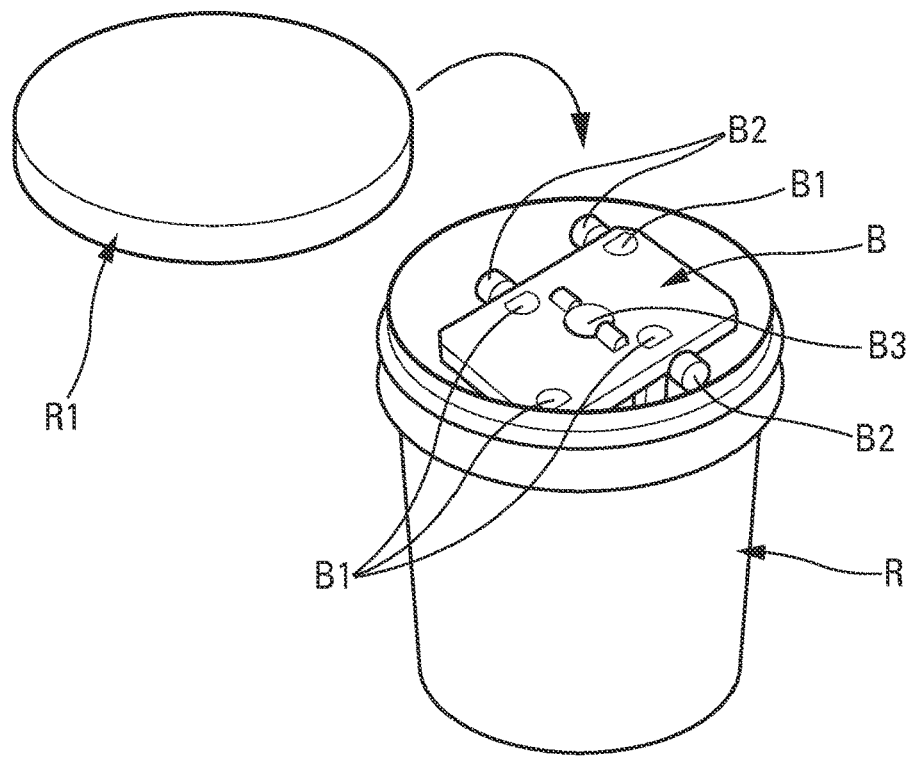
FIG. 4 is a perspective view of a container filled with inert gas in which the mounting slab with its implant support elements is placed.

In particular, it is possible to use the mounting slab B with its removable handle B4 during steps a- to e- of the method of grafting bioactive polymer. It is even possible to use the mounting slab B with its removable handle B4 so as to arrange the mounting slab B with its support elements S in the container filled with inert gas, such as argon. This can be seen in FIG. 4. The removable handle B4 needs to be removed, so as to leave its mounting housing B3 visible in the slab B. The container R may be closed by means of a lid R1: however, this is optional since argon is heavier than air and remains in the container R even in the absence of a lid. Thus, the mounting slab B with its four support elements S are put inside the polymerization chamber E that is filled with inert gas, such as argon, by being put into the container R. Inside the chamber E, the lid R1 can be removed and the mounting slab B with its support elements S can be extracted from the container R.

Figure 5A:
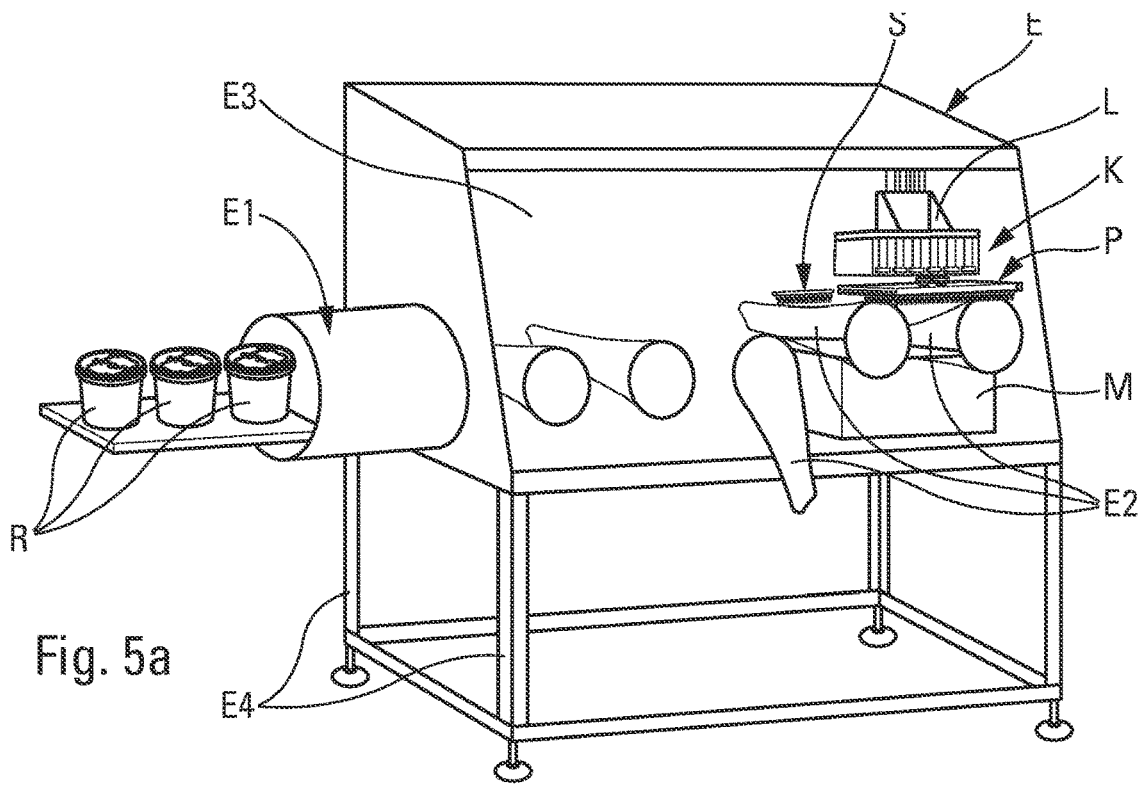
FIG. 5a is a diagrammatic perspective view of a chamber used for the polymerization step.

The polymerization chamber E can be seen in FIG. 5a. This type of chamber is commonly referred to as a "glove-box" because of the presence of gloves that make it possible to perform handling inside the chamber E through a transparent wall E3. Although not shown, the chamber E is provided with treatment means for treating its inside atmosphere, in order to guarantee optimum pressure, purity, and/or humidity conditions. The most commonly used gas is argon, although other gases may also be used. The chamber E is mounted on a stand E4 and includes an inlet air lock E1 through which the containers R pass so as to arrive inside the chamber E. In conventional manner, the air lock E1 includes an inlet door and an outlet door in order to be able to control the atmosphere that exists inside the air lock E1.

Figure 6:
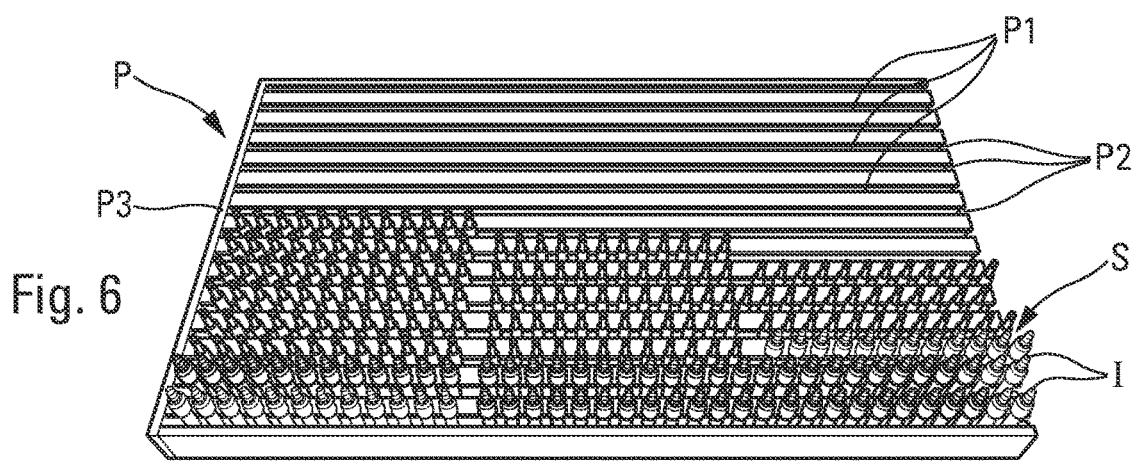
FIG. 6 is a perspective view of a mounting plate in which the implant support elements are received by sliding.

The polymerization chamber E contains a polymerization station K where the implants I are dipped in a polymerization bath so as to make it possible to synthesize bioactive polymers (e.g. PolyNaSS) on the anodized surface of the implants, from an appropriate monomer X, such as NaSS. The polymerization station K includes an elevator L that is movable vertically above a vessel T that is filled with monomer X, so as to dip the implants I into the polymerization bath of the vessel T and extract them therefrom. The polymerization station K advantageously includes catalyst means so as to accelerate polymerization on the implants dipped in the bath. The catalyst means may be in the form of a "bain-marie" tank M that is filled with liquid O that is heated by heater means M1, as can be seen in FIG. 6. The catalyst means may also take the form of a UV radiation source, as described below.

Figure 5B:
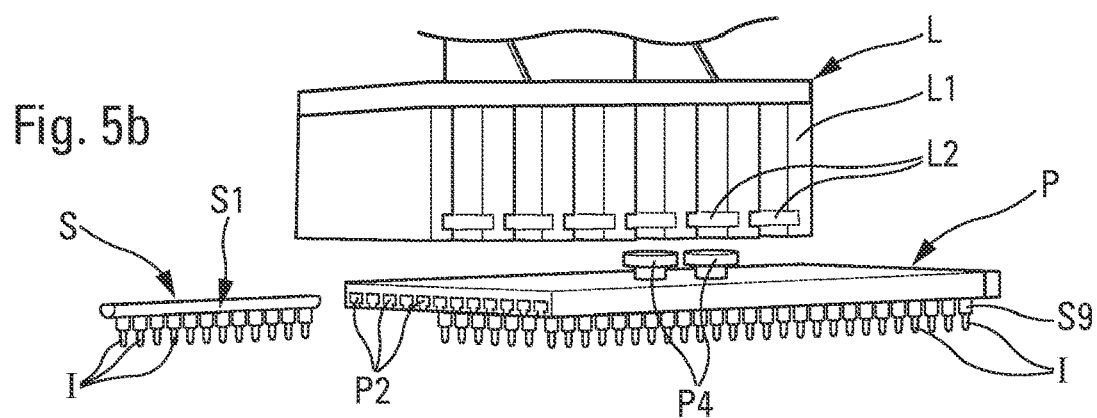
Figure 7:
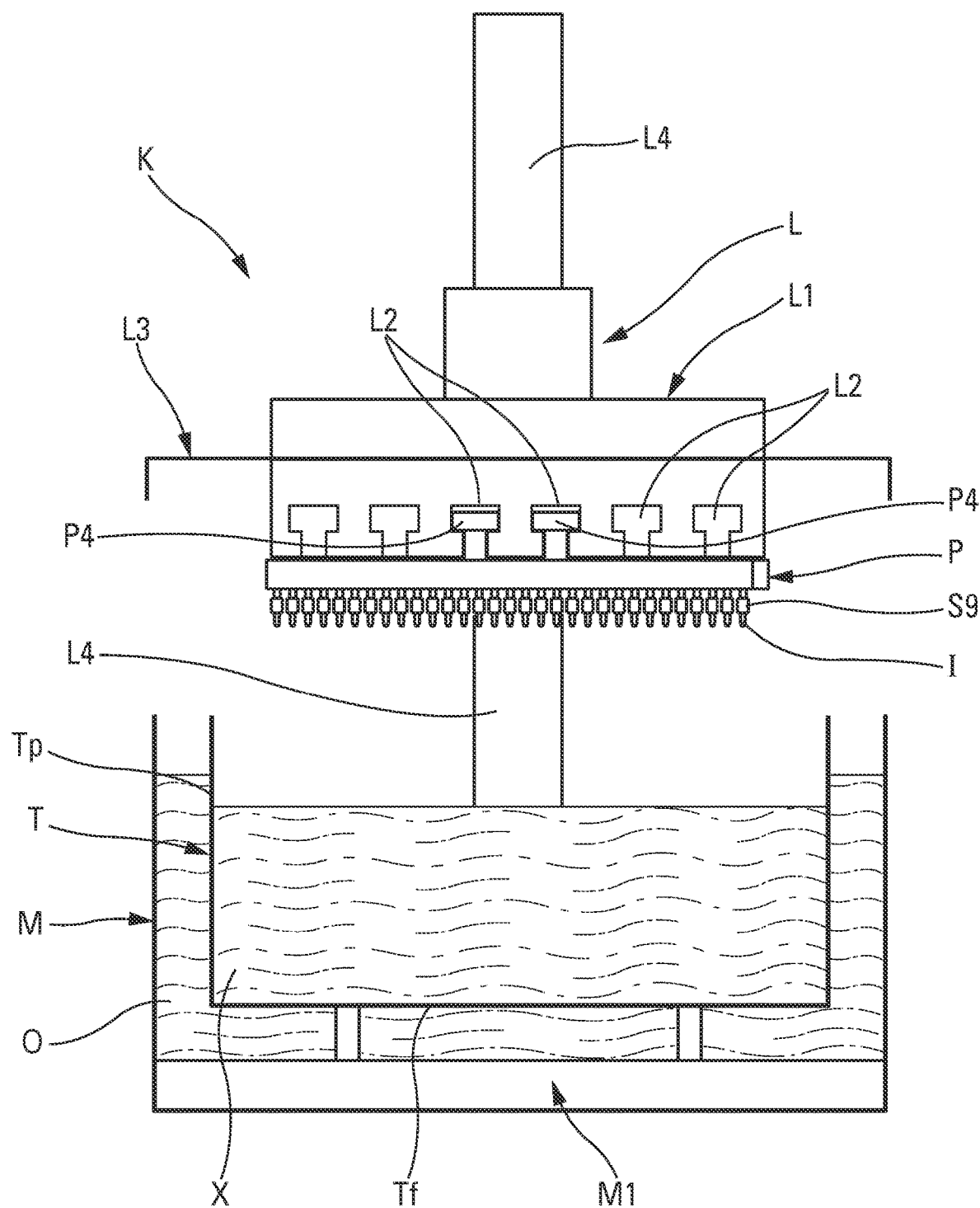
FIG. 7 is a diagrammatic plan view of the polymerization station arranged inside the polymerization chamber.

With reference simultaneously to FIGS. 5b, 6, and 7, it can be seen that the elevator L includes a carriage L1 that is movable vertically and that is mounted on a vertical rack L4 so as to make it possible to move the carriage L1 vertically down and up. The movable carriage is provided with mounting means that are suitable for receiving an implant support structure, as described below. By way of example, the mounting means may include a plurality of slideways L2 into which fastener means P4 of the support structure can be inserted by sliding. The slideways L2 form access openings on a front face that faces towards the glovebox gloves E2. The elevator L may optionally be provided with a lid L3 that covers, advantageously in leaktight manner, both the vessel T filled with monomer X and the bain-marie tank M filled with heated liquid O.

When the grafting method of the invention is applied to dental implants, and more particularly to support elements S as described above, a mounting plate P is provided that includes, on one of its faces, a plurality of mounting rails P1 that receive the bars S1 of the support elements S by sliding them into an open access end P2, as can be seen in FIG. 6. The support elements S may thus be received one behind another, and one beside another, in the mounting rails P1 of the mounting plate P until it is full. The pins S5 with their implants mounted thereon project out from the mounting rails P1. The mounting plate P is then turned upsidedown, and it may be mounted in the slideways L2 of the carriage L1 by means of one or more fastener lugs P4. In this way, the mounting plate P is fastened and arranged below the carriage L1. The elevator L may then be lowered, so as to dip the implants I into the bath of monomers X. The polymerization time lies in the range 2 hours (h) to 15 h as a function of the catalyst means used.

In a handling detail, the support elements S are removed from the support slab B while they are inside the chamber E, so as to be mounted individually in the mounting rails P1 of the support plate P.

By way of example, the vessel T in FIG. 7 that contains the monomer X may present a box shape, with a flat bottom Tf and four side walls Tp. With catalyst means in the form of a "bain-marie" tank M, this embodiment suffices. In order to make the temperature inside the tank of the vessel T uniform, flow-generator means may be provided, e.g. a stirring device.

Figure 8A:
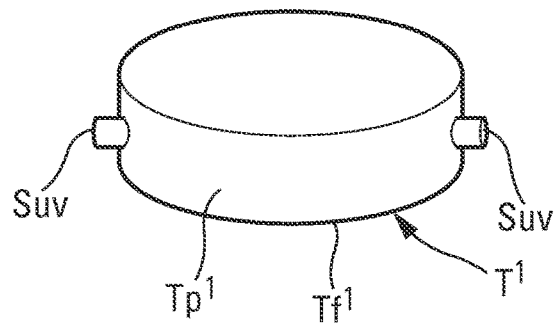
FIGS. 8a to 8e show various embodiments of a polymerization vessel containing the monomer.
Figure 8B:
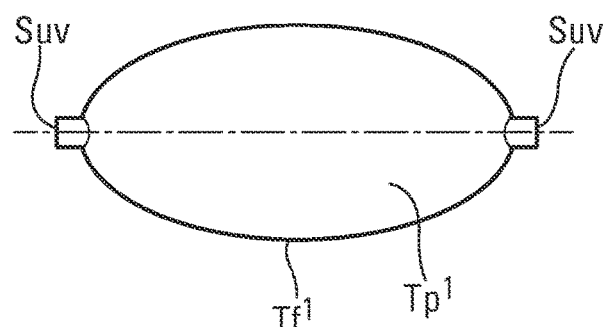

FIGS. 8a to 8e show, in very diagrammatic manner, a plurality of variant embodiments for a vessel filled with monomer X, and having catalyst means that are in the form of UV radiation sources. In FIGS. 8a and 8b, the vessel $T^1$ presents a flat bottom $Tf^1$, but presents a side wall $Tp^1$ that is elliptical in shape. Two UV radiation sources $S_{UV}$ are arranged one facing the other on the major axis of the ellipse, as shown in FIG. 8b. The elliptical shape of the side wall $Tp^1$ makes it possible to improve propagation of the UV radiation through the monomer, particularly when the side wall $Tp^1$, and possibly also the bottom $Tf^1$, are reflective. By way of example, it is possible to provide a vessel $T^1$ made of stainless steel with a mirror finish. It is also possible to provide a reflective silvered coating inside the vessel $T^1$.

Figure 8C:
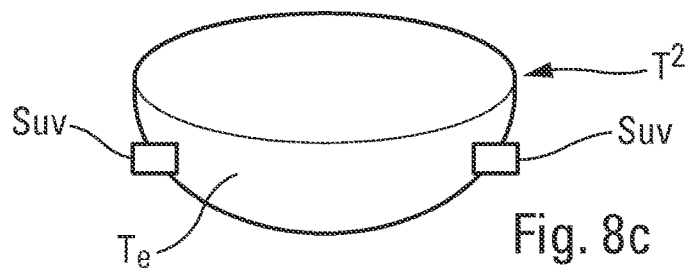

FIG. 8c shows a variant in which the vessel $T^2$ presents a wall Te in the shape of a dish or a trough, without a flat bottom. By way of example, it may correspond to a semicircular ellipsoid. Two UV radiation sources $S_{UV}$ are also arranged one facing the other on the major axis of the ellipsoid, as in the embodiment in FIGS. 8a and 8b.

Figure 8D:
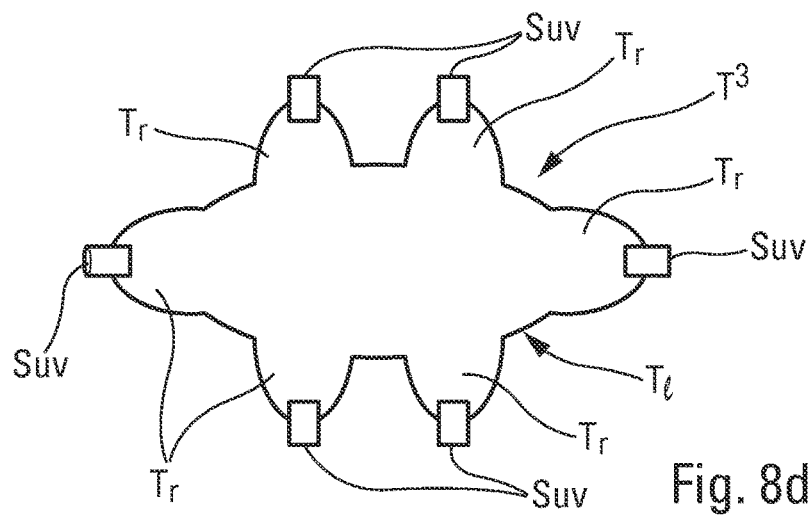

FIG. 8d shows yet another variant embodiment in which the vessel $T^3$ is made up of a plurality of elliptical reflectors Tr that are connected together by connection segments T1. The side wall of the vessel $T^3$ thus presents a complex shape. Each reflector Tr is provided with a UV radiation source $S_{UV}$. The side wall may be reflective, without a mirror finish or a silvered coating.

Figure 8E:
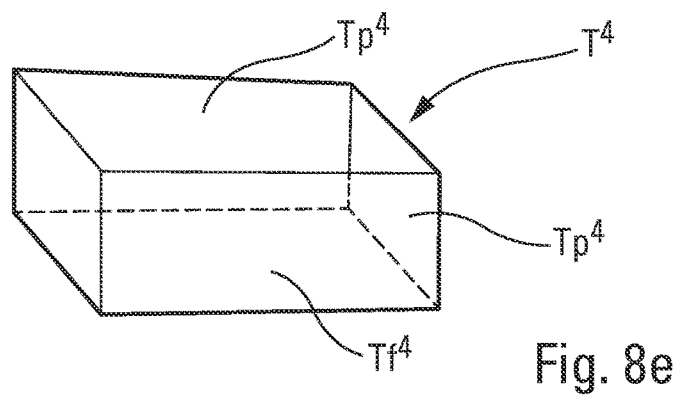

FIG. 8e shows another variant in which the vessel $T^4$ is box shaped, with a flat bottom $Tf^4$ and side walls $Tp^4$. One or more of the walls may be constituted by a UV panel. It is even possible to envisage that the entire vessel $T^4$ is constituted by five UV panels that are connected together.

Figure 10B:
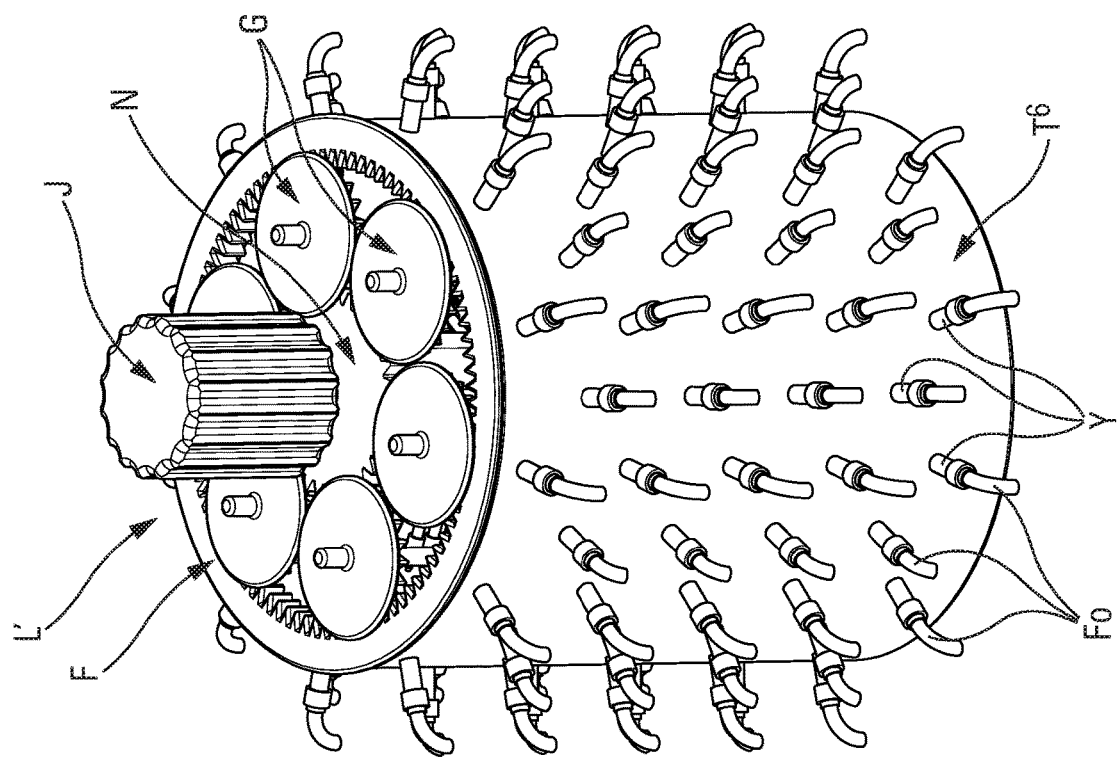
FIGS. 10a and 10b show two variants of vessels receiving the device in FIGS. 9a and 9b.
Figure 10A:
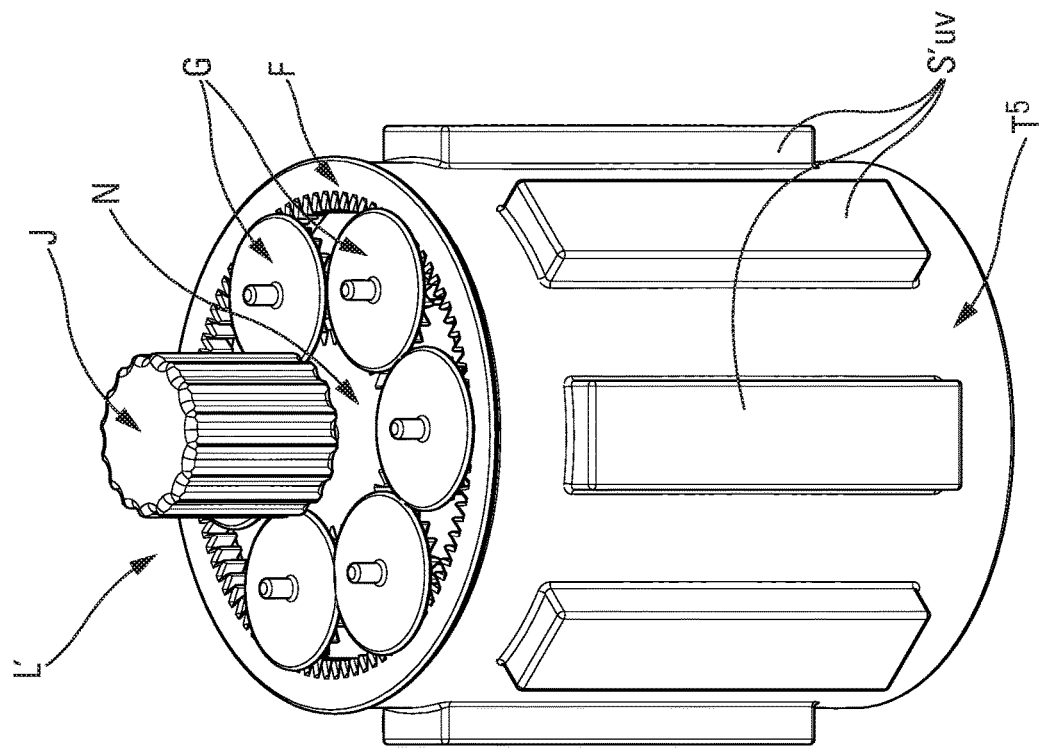

Reference is made to FIGS. 9a, 9b, 10a, and 10b in order to describe a second embodiment for a carriage L1' that can be used in the context of the present invention. The carriage L1' may be used in place of the above-described carriage L1 that is arranged inside the gastight chamber E. While the implants I are static in the vessel when the carriage L1 is in its low position, the implants I mounted on the carriage L1' are movable inside the vessel when the carriage L1' is in its low position. With reference to FIGS. 10a and 10b, it can be seen that the two versions of vessels $T^5$ and $T^6$ present a shape that is substantially cylindrical with UV radiation sources distributed over their peripheries. The vessel $T^5$ thus includes eight UV sources $S'_{UV}$ that are distributed in equidistant manner all around the vessel. The sources $S'_{UV}$ may present an axial extent that is large. The vessel $T^6$ is provided with a plurality of optical endpieces Y to which there are connected optical fibers Fo that are connected to a UV source (not shown). In view of the large number of endpieces Y and of optical fibers Fo, the inside of the vessel $T^6$ is irradiated in completely uniform manner. The inside wall of the vessels $T^5$ and $T^6$ may be reflective for UV radiation.

In FIGS. 10a and 10b, the carriage L1' is shown in its low position, in which it is inserted fully inside the vessels $T^5$ and $T^6$. In these figures, it is not shown how the carriage L1' is moved axially in a vertical direction, but any appropriate means can be used.

Reference is made below to FIGS. 9a and 9b in order to describe in detail the structure and the operation of the carriage L1'. In this embodiment, it is designed to receive support elements S as described above, but it could also be envisaged that support slabs B provided with a plurality of support elements S are received by the carriage L1'. In the particular configuration in FIGS. 9a and 9b, each support element S is mounted via its mounting end S4 at the free end of a vertical axial rod C that forms the rotary shaft of a horizontal wheel G. Each wheel G is provided with a top disk G1 through which the top end of the vertical axial rod C passes. In FIGS. 9a and 9b, the horizontal wheels G are six in number, but this number is not limiting. The horizontal wheels G are arranged inside a circularly-cylindrical collar F that is toothed internally at F1. Teeth G1 of the horizontal wheels G are engaged with the teeth F1 of the circularly-cylindrical collar F. The outer edge of each disk G2 bears against the circularly-cylindrical collar F. In addition, the toothed wheels G are also engaged with a central drive wheel N that is also toothed at N1. The top portion of the central wheel N is provided with a drive lug J for coming into engagement with rotary drive means (not shown). At its bottom end, the drive wheel N is provided with a hub Q that extends between the vertical axial rods C and the support elements S. Advantageously, the hub Q is reflective, very particularly to UV radiation. By way of example, it is possible to make the hub Q with reflective facets Q1. Although not shown, the carriage L1' may be provided with a cover that hermetically covers the horizontal wheels G and the circularly-cylindrical collar F.

With such a design, it can easily be understood that turning a drive lug J causes the drive wheel N to turn about its own axis. Given that the drive wheel N is in meshed engagement with the horizontal wheels G, the horizontal wheels turn both about their own axes, and also about the drive wheel N inside the circularly-cylindrical collar F. Consequently, the support elements S both turn about respective axes that pass via the rods C and their bars S1, and also revolve about a central axis that passes via the drive lug J, the drive wheel N, and the hub Q. The support elements S thus perform complex motion resulting from the combination of turning about their own bars and a revolving about the central drive wheel N. In this way, the implants I mounted on the support elements S move along complex paths inside the monomer present in the vessel. It is thus guaranteed that the implants I are exposed in identical and uniform manner to the UV radiation that irradiates the monomer present in the vessel.

With an elevator L' associated with a vessel irradiated by UV radiation, such as the vessels $T^5$ and $T^6$, a grafted coating of bioactive polymer, such as PolyNaSS, is obtained with the desired thickness and density. The time needed for satisfactory polymerization may be considerably shortened relative to polymerization with a thermal catalyst (of the "bain-marie" type), which is about 15 h. Specifically, it is easy to shorten the time by half, and by even more with UV radiation and a vessel that are optimized, so as to reach a time that lies in the range about 2 h to 5 h, or even less, of about 1 h.

Once grafting has been achieved, the implants are extracted from the vessel by raising the carriage L1 or L1'. The support elements S may then be removed from the carriage by handling them by means of the glovebox gloves E2. They may thus be put into the inlet air lock E1 from where they are extracted from the gastight chamber E. They may then be subjected to the steps of washing, so as to remove any excess grafted bioactive polymer, and drying.

Figure 11:
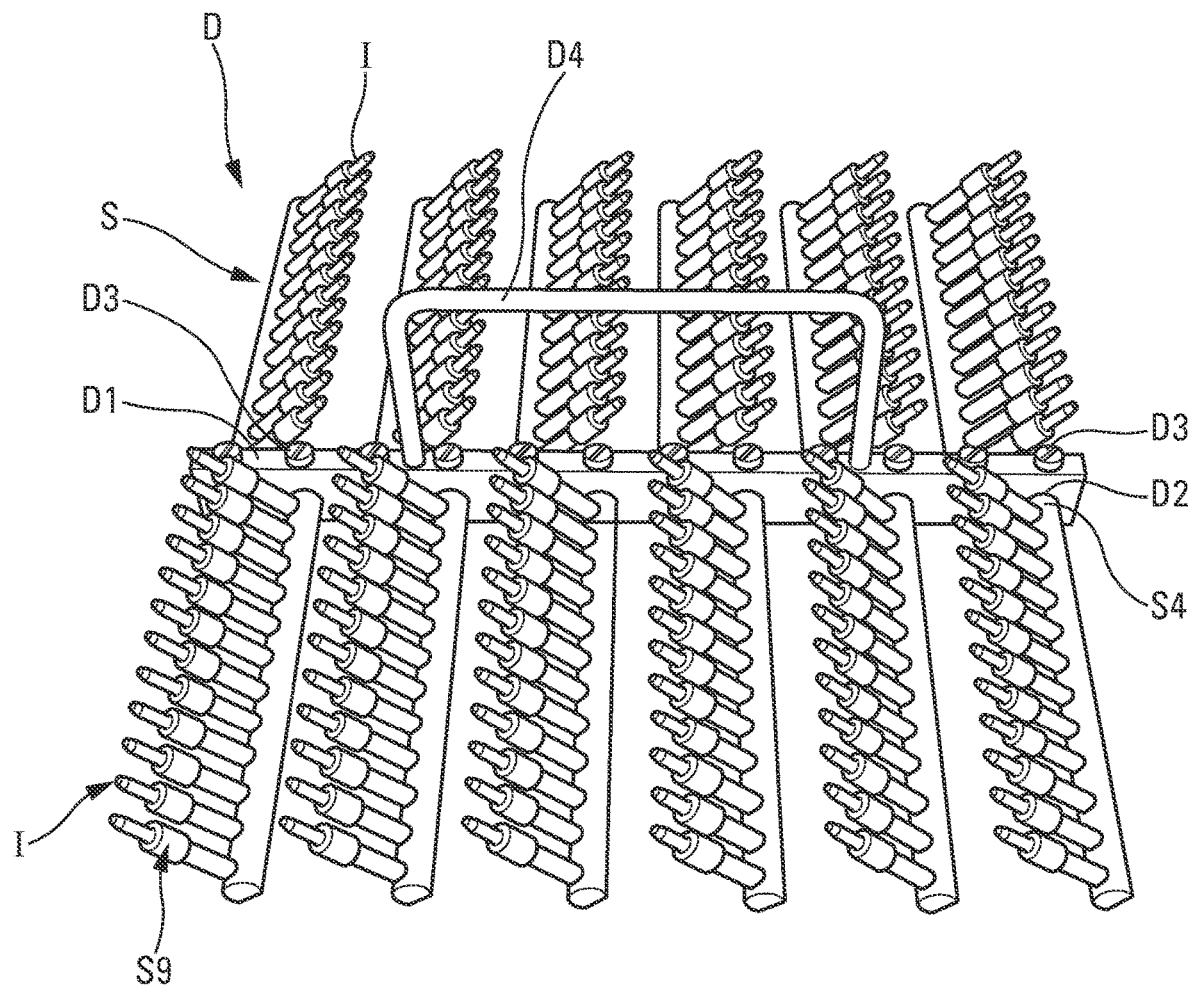
FIG. 11 is a perspective view of a washing rack of the invention.

FIG. 11 shows another utensil or instrument that makes it possible to advantageously handle support elements S during the washing and drying steps. The utensil may be referred to as a washing rack D, given that it presents a configuration that is close to the configuration of racks that are found in dishwashers. The washing rack D includes a central pole D1 that forms a plurality of mounting housings D2 in which the mounting ends S4 of the support elements S are received. Optional blocking screws D3 may be provided so as to block the mounting ends S4 inside the mounting housings D2. The central pole D1 may also be provided with a loop-shaped handle D4 via which the washing rack D can be gripped manually. In FIG. 11, twelve support elements S can be counted, namely six on each side of the central pole D1. It should be observed that the support elements S are arranged to slope by about 45° relative to the horizontal or the vertical. The slopes of the support elements S on either side of the central pole D1 are opposite, or offset by 90°. Specifically, the implants I visible below the central pole D1 in FIG. 11 point towards the left, while the implants I arranged above the central pole D1 point towards the right.

The washing rack D can thus easily be arranged in an appropriate washing appliance, into which water, preferably highly purified water, is sprayed over the implants I, in order to remove any excess grafted bioactive polymer therefrom. The washing stage is followed by a drying stage that may be performed in the same washing appliance.

At the end of the drying step, the rack D is extracted from the washing/drying appliance, and the support elements S are removed from the central pole D1. Then, the implants I may be removed from each support element S, as explained above, by turning the rotary rings S9 in order to unscrew the implants I from the threaded ends S8. Without going beyond the ambit of the invention, it is also possible to envisage that the implants I are held by suction on appropriate support elements.

The description above refers to a particular type of implant, namely dental implants I. However, the invention is not limited to that particular type of implant, and other types of implant may be processed, coated, and handled in accordance with the invention. With reference to FIGS. 12a to 12f, reference is made to another type of implant, namely a femoral hip implant H. It is also possible to refer to a femoral prosthesis. In typical manner, the insert H comprises a femoral pin H1 for being inserted and sealed in the femur, and a neck rod H2 for receiving the femoral head that is received in the acetabular cup fastened to the pelvis. The femoral prostheses H processed in this embodiment do not have heads.

Figure 12A:
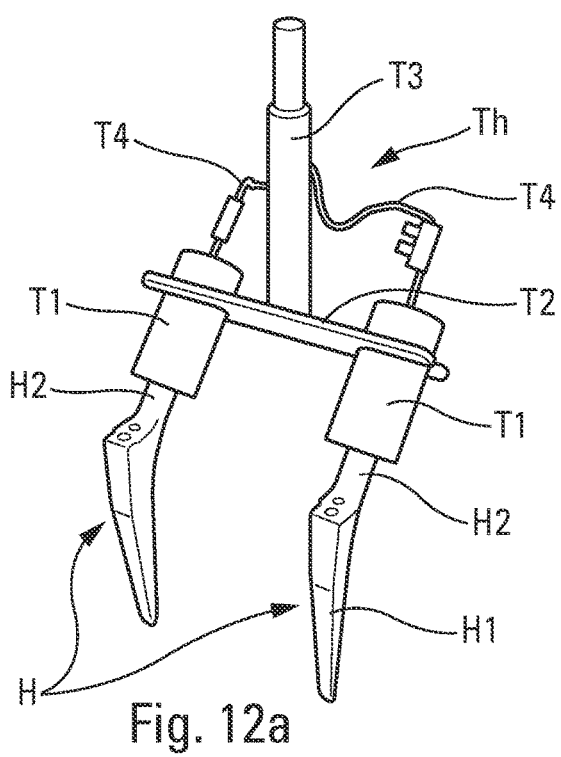
FIG. 12a shows a bracket for anodizing two femoral hip implants.
Figure 12B:
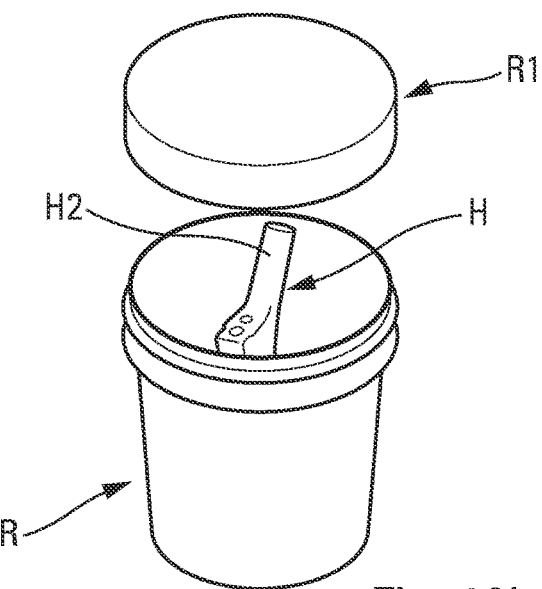
FIG. 12b shows a femoral hip implant arranged in a container filled with inert gas.

FIG. 12a shows a first support device in the shape of a bracket Th that makes it possible to receive two femoral implants H. More precisely, the bracket Th includes two reception sleeves T1 respectively receiving the neck rods H2 of the implants H. The sleeves T1 are mounted on a common plate that is provided with a mounting rod T3. The two sleeves T1 are also provided with electric wiring means T4 for supplying the inserts H with electricity. The bracket Th may be used during steps b, c, d, and e of the grafting method. The bracket Th constitutes an implant support structure, like the above-described support element S, support slab B, and support plate. The bracket Th may be mounted on an elevator by means of its mounting bar T3 so as to perform the cleaning, anodizing, and rinsing steps.

Figure 12C:
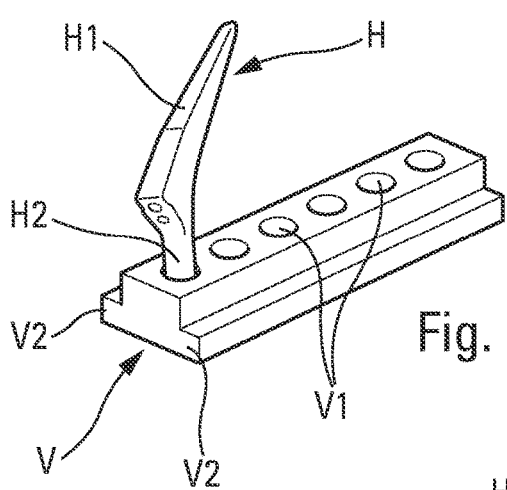
FIG. 12c shows a strip on which the femoral hip implants are mounted.
Figure 12D:
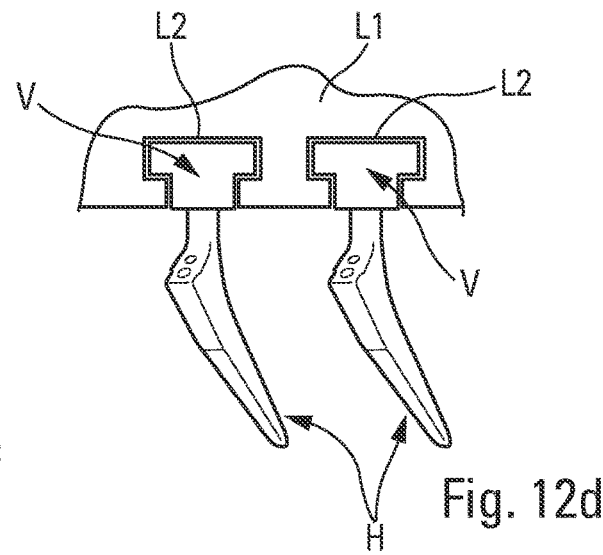
FIG. 12d shows two strips engaged in mounting rails of the elevator of the polymerization station.
Figure 12E:
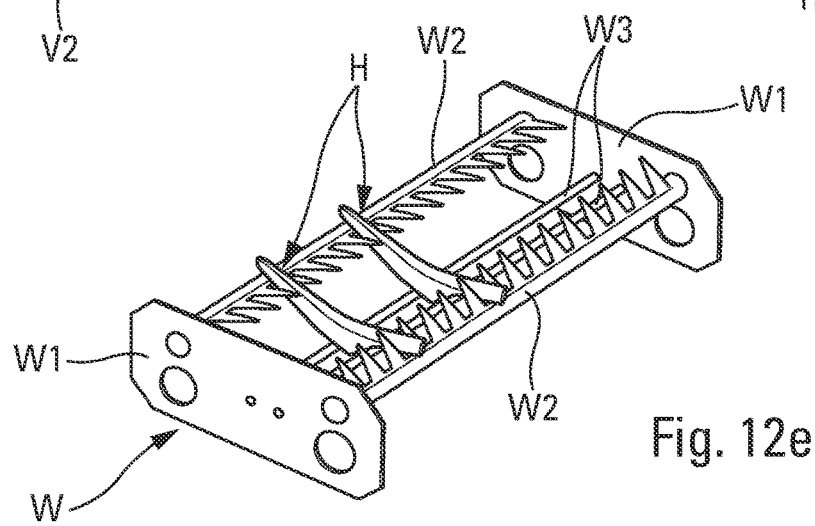
FIG. 12e shows a washing tray for femoral hip implants.

Once the steps have terminated, the implants H may be removed from the bracket Th and placed individually or as a group in a container R, such as the container used above for the dental implants. The container R is advantageously filled with an inert gas, such as argon, and it is optionally provided with a lid R1. The implants may thus be put into the polymerization chamber E through the inlet air lock E1. Inside the chamber, the implants H may be mounted on a strip V, as can be seen in FIG. 12c. The strip V includes reception holes V1 in which the neck rods H2 are force fitted. The strip V also includes two opposite longitudinal flanges V2 that make it possible to slide the strips V into slideways L2 of the carriage L1 of the elevator L, as can be seen in FIG. 12d. The implants H may thus be dipped into the vessel filled with monomer X. After sufficient polymerization time, the implants may be extracted from the vessel and the strips V may be extracted from the slideways L2. The implants H may then be removed from the strips V and extracted from the gastight chamber E through the inlet air lock. In a variant, the implants H may be mounted on the vertical axial rods C of the elevator L'. It can also be envisaged to mount a plurality of implants H on a single vertical axial rod C by using a support structure, such as the bracket Th.

For the subsequent washing and drying steps, a washing tray W is provided (FIG. 12e) on which the grafted implants may be arranged. The washing tray W comprises two end flanges W1 that are connected together via two separator rakes W2 and two support rods W3. The implants H may thus be arranged between the teeth of the rakes W2 and bear against the support rods W3.

It should be observed that certain particular aspects associated with handling femoral implants H may be protected independently of other characteristics described above, and could as a result be the subject of divisional applications. More particularly, the bracket Th, the strip V, and the washing tray W could be the subject of their own patent applications.

The invention thus provides a method of grafting bioactive polymer onto implants that may be performed industrially on a very large scale. The utensils that have been designed, such as the support element S, the support slab B, the support plate P, the washing tray D, the support bracket Th, the strip V, and the washing tray W make it possible to optimize the grafting method on an industrial scale. Finally, the gastight chamber E, and more particularly its carriage and its vessel make it possible to perform the polymerization step on a large scale. Implants, in particular dental and hip implants, may thus be coated with a bioactive polymer, such as PolyNaSS, on a large scale and at a high rate.

The invention claimed is:

1. A method of grafting PolyNaSS on implants made of titanium or titanium alloy on an industrial scale, the method comprising the following successive steps:
   a) mounting implants on an implant support structure;
   b) dipping the implants into a bath of acid so as to clean them;
   c) rinsing the implants;
   d) dipping the implants in an anodizing bath so as to anodize them;

e) rinsing the implants;
f) putting the implants into a polymerization chamber filled with inert gas;
g) mounting the implants on an elevator present in the polymerization chamber;
h) actuating the elevator $(L; L')$ so as to dip the implants (I; H) into a polymerization bath present in the polymerization chamber;
i) subjecting the polymerization bath to a polymerization catalyst so as to synthesize PolyNaSS on the implants;
j) raising the elevator so as to extract the implants from the polymerization bath;
k) removing the implants from the elevator;
l) extracting the implants from the chamber;
m) washing the implants so as to remove any excess non-grafted PolyNaSS therefrom; and
n) drying the grafted implants; and
wherein the method further comprises an intermediate step a1- between step a- and step b-, step a1- comprising mounting a plurality of implants on support elements that are themselves mounted on a support slab that includes a removable handle.

2. The method according to claim 1, wherein, during steps b- to f-, the implants are handled by means of the support slab.

3. The method according to claim 2, further comprising an intermediate step e1- between step e- and step f-, step e1- comprising placing the support slab with its support elements for supporting implants in a container filled with inert gas, the container then being put, during step f-, into the polymerization chamber filled with inert gas, the container then being opened so as to extract the support slab therefrom, together with its support elements for supporting implants.

4. The method according to claim 3, further comprising an intermediate step f1- between step f- and step g-, step f1- comprising removing the implant support elements from the support slab, then in mounting the support elements for supporting implants on a support plate that is then mounted on the elevator.

5. The method according to claim 4, further comprising an intermediate step k1- between step k- and step f-, step k1- comprising removing the support elements for supporting implants from the elevator, then in mounting the support elements for supporting implants on a central pole that forms mounting housing for the support elements for supporting implants in order to form a washing rack that is then extracted from the polymerization chamber.

6. The method according to claim 5, wherein, during steps m- and n-, the support elements for supporting implants are configured in the form of the washing rack.

7. The method according to claim 3, wherein the inert gas in intermediate step e1 is argon and the inert gas in step f is argon; and wherein the container filled with the inert gas in intermediate step e1 is provided with a gastight lid.

8. The method according to claim 3, further comprising an intermediate step f2- between step f- and step g-, step f2- comprising mounting either the support slab or the support elements on vertical axial rods of the elevator that are rotated and revolve in the polymerization bath.

9. The method according to claim 1, wherein the inert gas in step t is argon.

10. A method of grafting PolyNaSS on implants made of titanium or titanium alloy on an industrial scale, the method comprising the following successive steps:
a)) mounting implants on an implant support structure;
b) dipping the implants into a bath of acid so as to clean them;
c) rinsing the implants;
d) dipping the implants in an anodizing bath so as to anodize them;
e) rinsing the implants;
f) putting the implants into a polymerization chamber filled with inert gas;
g) mounting the implants on an elevator present in the polymerization chamber;
h) actuating the elevator so as to dip the implants into a polymerization bath present in the polymerization chamber;
i) subjecting the polymerization bath to a polymerization catalyst so as to synthesize PolyNaSS on the implants;
j) raising the elevator so as to extract the implants from the polymerization bath;
k) removing the implants from the elevator;
l) extracting the implants from the chamber;
m) washing the implants so as to remove any excess non-grafted PolyNaSS therefrom; and
n) drying the grafted implants; and
wherein the method further comprises an intermediate step a2- between step a- and step b-, step a2- comprising mounting a plurality of implants on a support bracket, the implants, being handled, during steps b- to f-, by means of the support bracket.

11. The method according to claim 10, further comprising an intermediate step f3- between step f- and step g-, step f3- comprising mounting the implants side-by-side on a strip that is then mounted on the elevator.

12. The method according to claim 11, wherein, during step f-, the implants are on the strip.

13. The method according to claim 10, wherein, during steps m- and n-, the implants are arranged on a washing tray.

* * * * *